US 6,547,852 B2
Apr. 15, 2003

(54) TRANSVERSE THERMAL MODULATION

(75) Inventors: Edward B. Ledford, Jr., Lincoln, NE (US); Chris A. Billesbach, Lincoln, NE (US); Joel R. Termaat, Lincoln, NE (US)

(73) Assignee: Zoex Corporation, Lincoln, NE (US)

( * ) Notice: Subject to any disclaimer, the term of this patent is extended or adjusted under 35 U.S.C. 154(b) by 0 days.

(21) Appl. No.: 09/760,508

(22) Filed: Jan. 12, 2001

(65) Prior Publication Data

US 2001/0037727 A1 Nov. 8, 2001

Related U.S. Application Data

(60) Provisional application No. 60/175,727, filed on Jan. 12, 2000.

(51) Int. Cl.$^7$ ............................................... B01D 15/08
(52) U.S. Cl. ............................................ 95/87; 96/101
(58) Field of Search ................... 95/82–87; 96/101–107

(56) References Cited

U.S. PATENT DOCUMENTS

| | | | |
|---|---|---|---|
| 3,043,127 A | | 7/1962 | Ford et al. ..................... 73/23 |
| 3,057,183 A | | 10/1962 | Ford ............................. 73/23 |
| 3,305,000 A | * | 2/1967 | Bullen et al. ............. 96/102 X |
| 3,309,504 A | * | 3/1967 | Rosso et al. ............. 96/104 X |
| 4,923,486 A | | 5/1990 | Rubey ............................ 55/67 |
| 4,948,389 A | * | 8/1990 | Klein et al. ................ 95/87 X |
| 5,135,549 A | | 8/1992 | Phillips et al. .................. 55/67 |
| 5,196,039 A | | 3/1993 | Phillips et al. .................. 55/67 |
| 5,215,556 A | * | 6/1993 | Hiller et al. .................... 95/87 |
| 5,341,578 A | | 8/1994 | Anderson ...................... 34/97 |
| 5,402,936 A | | 4/1995 | Hammelmann .......... 239/263.1 |
| 5,547,497 A | | 8/1996 | Klemp et al. ................. 96/104 |
| 5,596,876 A | * | 1/1997 | Manura et al. ............. 95/87 X |
| 5,929,321 A | | 7/1999 | Bertrand .................... 73/23.39 |
| 6,007,602 A | | 12/1999 | Ledford, Jr. et al. ............. 95/8 |
| 6,190,613 B1 | * | 2/2001 | Watanabe et al. .......... 95/87 X |

FOREIGN PATENT DOCUMENTS

| | | | |
|---|---|---|---|
| EP | 0 051 778 A2 | 5/1982 | .......... G01N/31/08 |
| EP | 0 459 677 A2 | 12/1991 | .......... G01N/30/46 |
| EP | 0 522 150 B1 | 12/1998 | ........... B01D/15/08 |

OTHER PUBLICATIONS

Kinghorn et al., *Enhancement of Signal–to–Noise Ratios in Capillary Gas Chromatography by Using a Longitudinally Modulated Cryogenic System*, J. High Resol. Chromatogr., vol. 21, pp 32–38 (Jan. 1998).

(List continued on next page.)

Primary Examiner—Robert H. Spitzer
(74) Attorney, Agent, or Firm—Kilyk & Bowersox, P.L.L.C.

(57) ABSTRACT

A method of thermally modulating a tubular member carrying a sample substance therethrough is provided. The method includes the steps of (a) directing at least one gas stream toward a tubular member in a direction substantially transverse to the tubular member, wherein the temperature of the gas stream differs from the temperature of the tubular member; and (b) varying the gas flow rate of the at least one gas stream as a function of time to thermally modulate the tubular member. An apparatus is also provided for thermal modulation and includes: a tubular member for carrying a sample substance therethrough in a fluid medium; a gas stream source for directing a gas stream toward the tubular member in a direction substantially transverse to the tubular member; a gas stream supplied from the source with a temperature that differs from the temperature of the tubular member; and a gas stream of varying gas flow rate supplied from the gas stream source as a function of time to thermally modulate the tubular member.

26 Claims, 4 Drawing Sheets

OTHER PUBLICATIONS

Van Es et al., *Sample Enrichment in High Speed Narrow Bore Capillary Gas Chromatography*, J. High Resol. Chromatogr., vol. 11, pp 852–857 (Dec. 1988).

Liu et al., *Large–Volume Sample Introduction into Narrow–Bore Gas Chromatography Columns Using Thermal Desorption Modulation and Signal Averaging*, J. Microcol. Sep., vol. 2, No. 1, pp 33–38 (1990).

Springston, *Cryongenic–focusing, ohmically heated on–column trap for capillary gas chromatography*, Journal of Chromatography, 513, 517, pp 67–75 (Sep. 26, 1990).

Phillips et al., *Thermal Modulation for Sample Introduction into Ultra–small Diameter Capillary Columns in GC*, International Symposium on Capillary Chromatography, 10632, 11, pp 474–481 (May 14–17, 1990).

Liu et al., *High–Speed Gas Chromatographic Analysis of a Simulated Process Stream using On–Column Thermal Desorption Modulation for Sample Preconcentration and Introduction*, Journal of Chromatographic Science, vol. 28, pp 567–571 (Nov. 1990).

Marriott et al., *trends in analytical chemistry*, vol. 18, No. 2, pp 115–125 (1999).

\* cited by examiner

000107_kero_R2_proc.bin   DB-1   4.0m   90min

000107_kero_R2_proc.bin   Db-1   4.0m   90min

TRANSVERSE THERMAL MODULATION

CROSS REFERENCE TO RELATED APPLICATION

This application claims the benefit under 35 U.S.C. §119 (e) of prior U.S. Provisional Application No. 60/175,727 filed Jan. 12, 2000, which is incorporated in its entirety by reference herein.

BACKGROUND OF THE INVENTION

In the art of gas chromatography, the process of thermal modulation has made possible comprehensive multi-dimensional separation techniques that have revealed startling complexity in many chemical mixtures, especially petroleum and petroleum-derived liquids.

In the prior art, thermal modulation methods have comprised the steps of heating sections of capillary columns with electrically pulsed resistive films, or the creation of heated or cooled zones moving in a longitudinal direction along segments of columns, the movement of the zones being mediated by mechanical devices. Resistive heating techniques, and mechanically swept heating techniques are described in U.S. Pat. No. 5,196,039 to Phillips et al, and U.S. Pat. No. 6,007,602 to Ledford, Jr. et al, and in European Patent Specification No. EPO 522 150 B1 corresponding to PCT publication WO 92/13622, all of which are incorporated herein in their entireties by reference. Longitudinally translated cooling techniques are described by Marriot in P. Marriot, and R. Kinghorn, *Trends in Analytical Chemistry*, 1999, 18, 114, which is also incorporated herein in its entirety by reference.

Mechanical translation techniques have the advantage of being more robust and reliable than resistive heating techniques. Mechanical translation techniques employed in the prior art have certain disadvantages however. In general, moving heaters or coolers are undesirable in that they make for complex apparatus prone to various forms of mechanical failure. The positioning of columns in mechanically translated heaters and coolers is inconvenient. The inertia of mechanically translated heaters and coolers sets limits on the frequency of thermal modulation. This is a severe limitation, since higher dimensional chromatographic techniques, such as three-dimensional gas chromatography, benefit from high frequency thermal modulation. Prior art embodiments also have employed the ambient stirred oven bath of the gas chromatograph to heat or cool sections of the modulator tube. The heating and cooling rates derived from the stirred oven bath set limits on minimum achievable chemical pulse widths, hence the frequency of thermal modulation.

SUMMARY OF THE INVENTION

The art of thermal modulation is considerably improved by the method of the present invention wherein heating and cooling segments of modulator tubes achieve modulation frequencies in the range of 2 Hz to 20 Hz. The method entails no moving parts in the vicinity of the modulator tube and does not present difficulties with respect to aligning the modulator tube with heating and cooling means.

The present invention provides an apparatus and method of thermal modulation that includes directing jets of gas flowing substantially perpendicular to a modulator tube in a chromatographic separation device, and preferably comprises directing pulsed jets of gas perpendicular to a gas chromatographic modulator tube. The apparatus of the present invention provides means to direct jets of gas substantially perpendicular to a modulator tube and preferably provides means to supply pulsed jets of gas. A surprising result is that even within the stirred oven bath of a gas chromatograph, the jets can heat and cool segments of a modulator tube at least 2.0 cm away from a nozzle exit orifice to temperatures, and at thermal heating and cooling rates, suitable for high speed thermal modulation. The ambient oven bath, even though it is strongly stirred by means of a fan inside the GC oven, does not interfere with the cooling or heating action of the gas jets directed onto the modulator tube. Because gas jets are spatially diffuse, and nozzles may be physically distant from the modulator tube, the act of mounting the modulator tube in the path of the gas jets is far more straightforward than prior art techniques for aligning modulator tubes with mechanically rotated or translated heating and cooling means, an important matter from the standpoint of ease of use and commercialization.

Herein, the present method of thermal modulation by means of gas jets directed substantially perpendicular to a modulator tube in a chromatographic apparatus are referred to as methods of "transverse thermal modulation", or more simply, "transverse modulation." The advantages of transverse thermal modulation will become more apparent in view of a detailed description of the method with reference to FIG. 1, which represents one embodiment of the present invention as it would be employed in a comprehensive two-dimensional gas chromatograph.

It is to be understood that both the foregoing general description and the following detailed description are exemplary and explanatory only and are intended to provide further explanation of the present invention, as claimed.

BRIEF DESCRIPTION OF THE DRAWINGS

The invention will be described in more detail with reference to the accompanying figures, wherein.

DETAILED DESCRIPTION OF THE INVENTION

Figure 1:
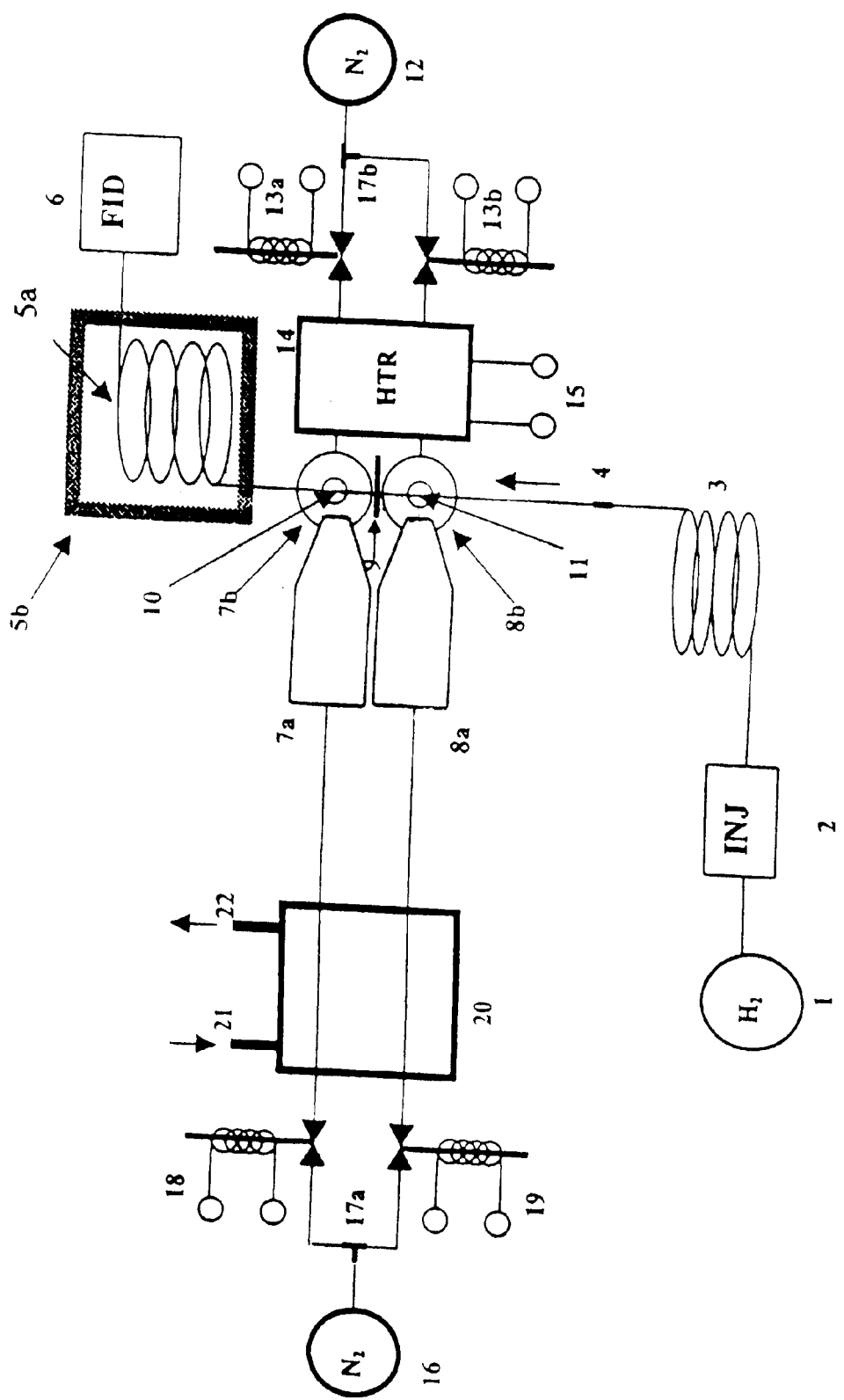
FIG. 1 is a schematic diagram of a gas chromatographic apparatus according to an embodiment of the present invention.

The present invention is exemplified in the apparatus shown in FIG. 1. A source of carrier gas 1, typically hydrogen, supplies an injector 2, connected to a first capillary column 3, a butt connector 4, a second capillary column 5a, and a detector 6. The detector can be, for example, a flame ionization detector (FID). Gas nozzles 7a, 7b, 8a, and 8b direct transverse gas flows of gas onto the head of the secondary column 5a, thereby forming thermal zones 10 and 11 which may be alternately cooled and heated in a manner known to produce thermal modulation. Zones 10 and 11 form the second and first stages, respectively, of a two-stage thermal modulator. In the embodiment shown in FIG. 1, the nozzles 7b and 8b are shown in end view, their gas streams being directed toward the reader. Nozzles 7b and 8b are used to heat the first stage 11 and the second stage 10 of the thermal modulator. These nozzles are supplied with a gas flow, typically nitrogen, from a reservoir 12 through a tee connection 17b and solenoid valves 13a and 13b, which are used to pulse the gas flow to the nozzles 7b and 8b. Gas exiting valves 13a and 13b passes through a heater 14 receiving electrical voltage at contacts 15, which heats the flow of gas to nozzles 7b and 8b. Nozzles 7a and 8a are used to direct cooled gas onto modulator stages 10 and 11. These nozzles are supplied with gas, typically nitrogen, from a reservoir 16, which via a tee-connection 17a, flows to solenoid valves 18 and 19. These valves pulse the gas stream through a heat exchanger 20 equipped with an inlet port 21 and an outlet port 22 through which a refrigerating fluid, typically liquid nitrogen boiloff, is passed. The refrigerating fluid cools the gas streams supplied to nozzles 7a and 8a. The hot jets 7b and 8b are of larger diameter than the cold jets 7a and 8a, thereby causing the heated regions of the modulator stages to overlap the cooled regions of the modulator stages. This measure prevents any possibility of a cold spot in the modulator, which would corrupt thermal modulation. The hot gas streams are separated by a baffle 9, typically made of a thin aluminum plate, which prevents the upstream hot jet 8b from heating the downstream thermal modulator stage 10, and the downstream hot jet 7b from heating the upstream thermal modulator stage 11.

In practice, the hot jet assembly and the cold jet assembly are mounted in separate aluminum blocks separated by steel roll pins in a manner commonly known in the mechanical arts. This mechanical separation is also thermal separation, which makes it possible to maintain the hot and cold jet assemblies at different temperatures, a temperature difference of more that 200 degrees Celcius being common. In operation, a sample containing a mixture of chemical substances is injected at injector 2, and undergoes chromatography in column 3. Valves 13a, 13b, 18, and 19 are actuated in opposition such that thermal modulator stages 10 and 11 are alternately cooled and heated, in the manner of two-stage thermal modulation known in prior art. Chemical pulses from the thermal modulator undergo additional chromatography in the second column 5a, and proceed to detector 6 that registers a comprehensive two-dimensional chromatogram.

The secondary column 5a is housed in a separate thermal chamber 5b in order to permit thermal decoupling from the first column 3. This measure aids in tuning the instrument. The secondary thermal chamber 5b may lead, equal, or lag the temperature of the first column during temperature-programmed runs. When the temperature of chamber 5b leads the temperature of the first column, it is sometimes desirable to connect the second column to the detector and the modulator tube with uncoated capillary transfer lines. In that case, the stationary phase in the modulator tube should terminate within the cooled region of the second stage of the thermal modulator. This measure prevents broadening of modulated peaks, which might occur on the length of tubing connecting the thermal modulator to the secondary chamber 5b, whenever the temperature of the latter leads the temperature of the first column 3.

Columns 3 and 5a may be mounted in the GC oven using common methods known in chromatographic or mechanical arts. The head of the second column, which may serve as a modulator tube, is mounted by means of bulkhead fittings common in chromatographic art, so that the column is held within the exit gas streams of nozzles 7a, 7b, 8a, and 8b. The bulkhead fittings are typically spring loaded so as to tension the modulator tube slightly when it is positioned in the exit streams of the gas nozzles. This measure prevents bowing of the modulator tube during oven temperature cycling.

Figure 2:
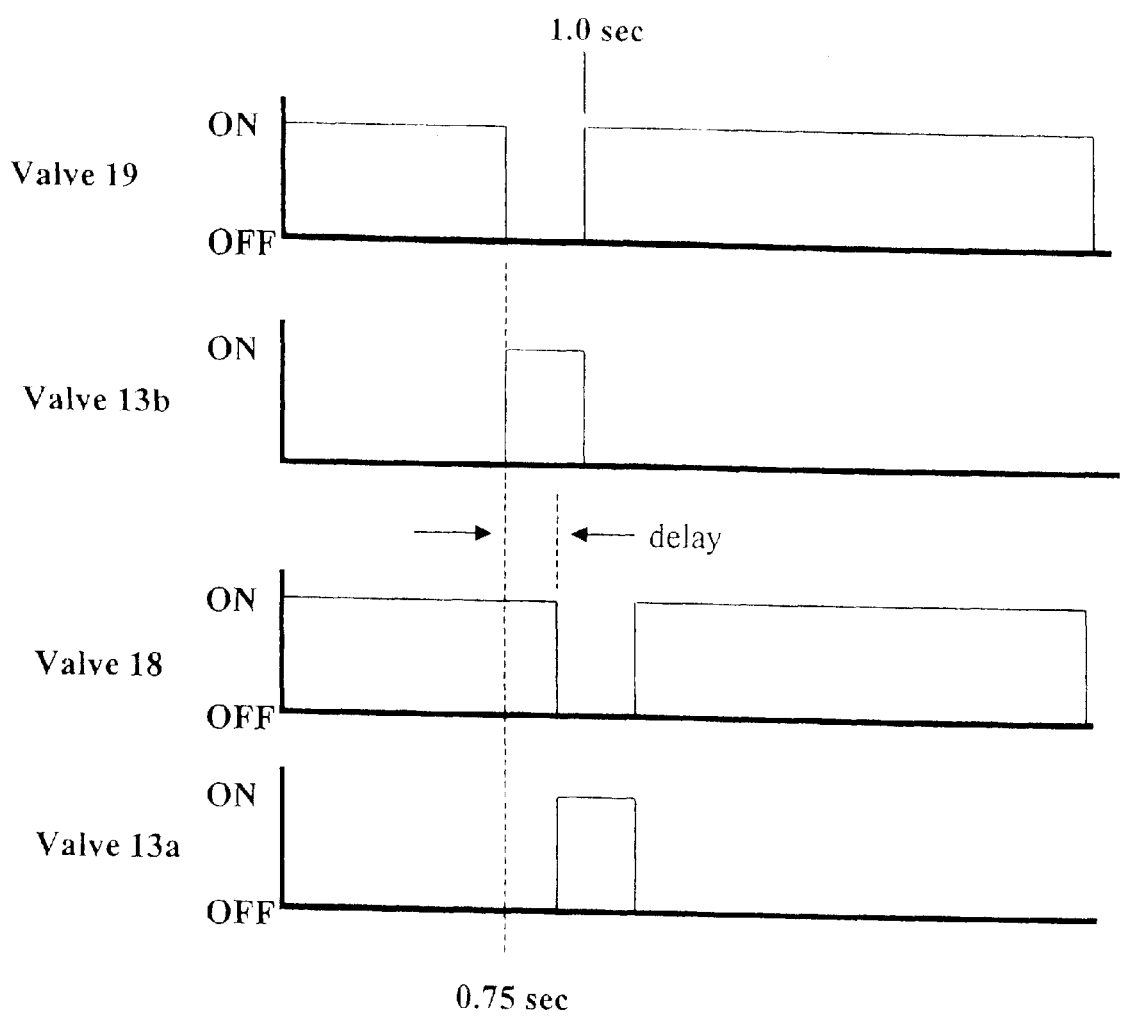
FIG. 2 is a diagram showing the temporal sequence of valve actuation for the valves shown in the apparatus of FIG. 1.
Figure 3A:
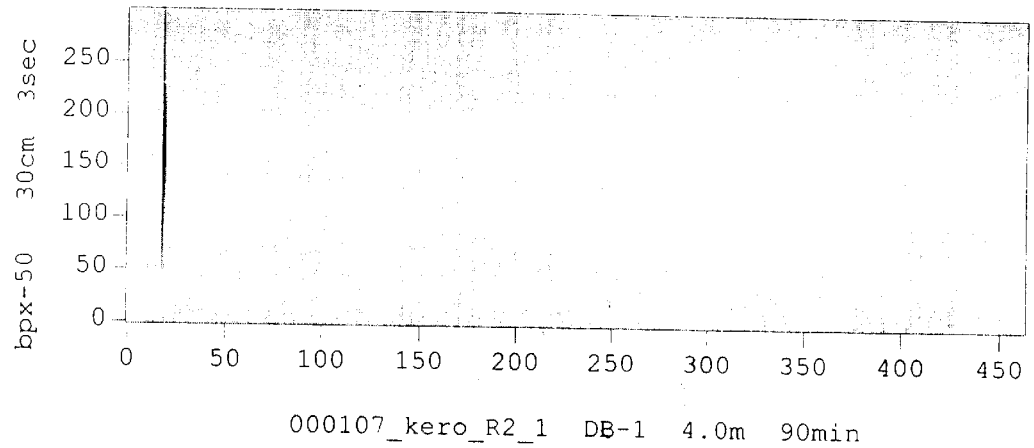
FIGS. 3A–3D are portions of a common gas chromatogram obtained from the apparatus depicted in FIG. 1 using a method according to the present invention.
Figure 3B:
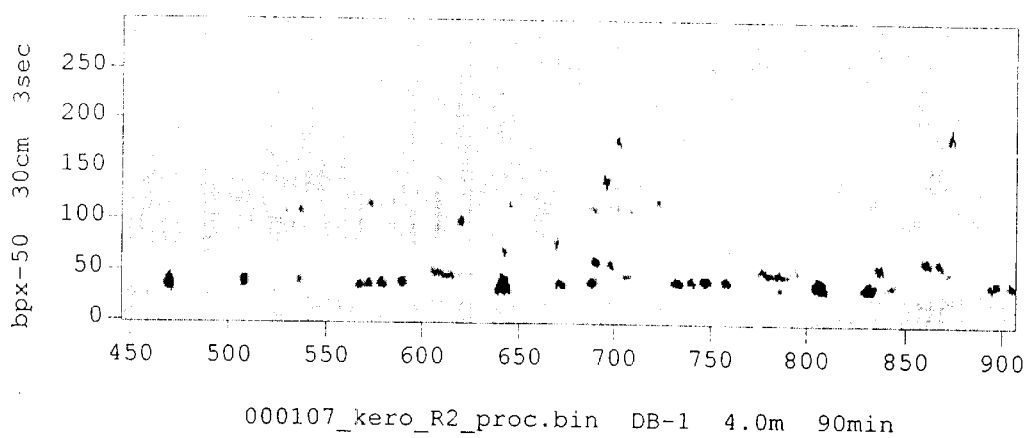
Figure 3C:
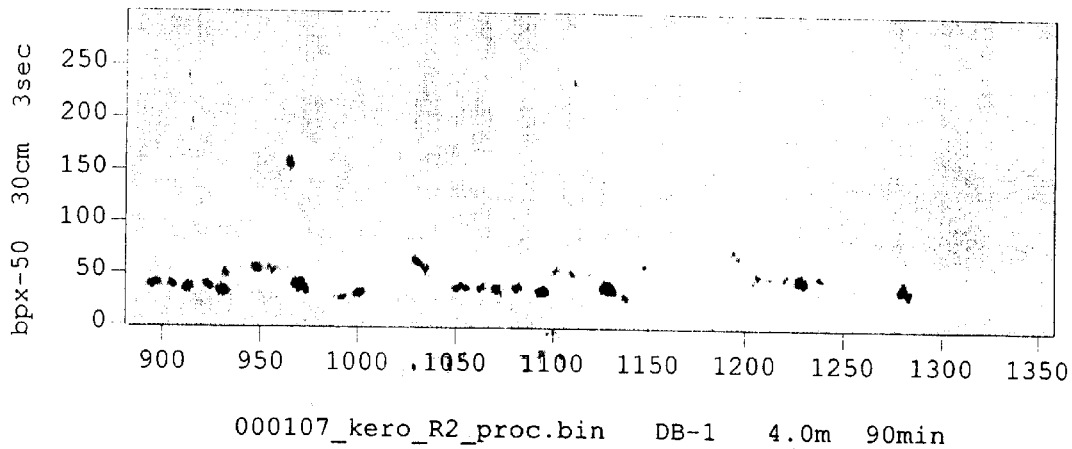
Figure 3D:
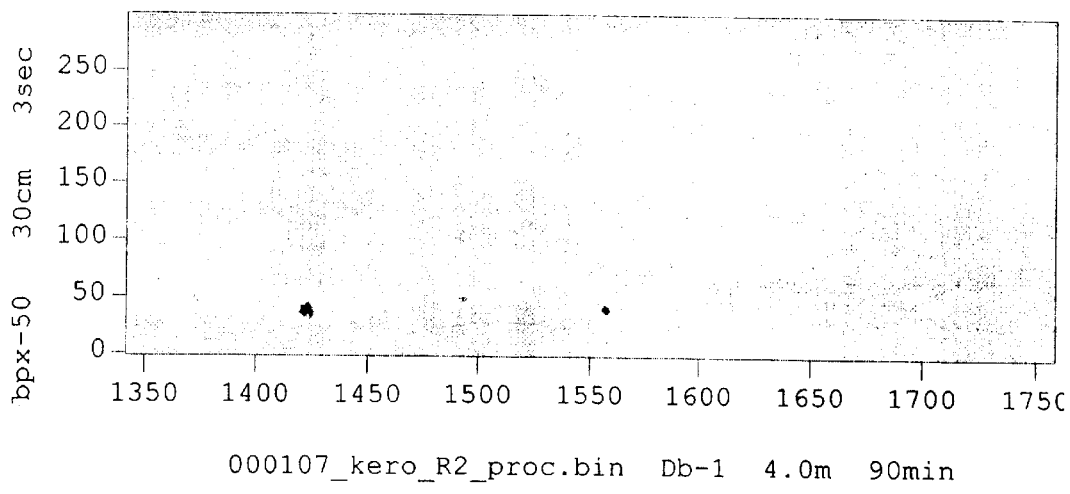

More detailed understanding of the method of transverse thermal modulation follows from consideration of FIG. 2, which represents a temporal sequence in which valves 13a, 13b, 18, and 19 are actuated so as to produce one cycle of two-stage thermal modulation.

As shown in FIG. 2, valves 18 and 19 are initially turned on, while valves 13a and 13b are turned off for a period of time, which may be, for example, approximately 0.75 seconds. Then the states of valves 19 and 13b are switched for a period of time, which may be, for example, from about 0.15 to about 0.35 second, such as about 0.25 second. After a delay, which may be, for example, from about 0.020 to about 0.080 second, such as about 0.050 second, in duration, the states of valves 18 and 13a are switched for a period of time, which may be, for example, from about 0.1 to about 0.5 second, such as about 0.25 second. This sequence of valve states causes first the upstream modulator stage 11 to be heated from an initially cooled state, followed by heating of the downstream modulator stage 10 from an initially cooled state, thereby effecting a thermal modulation. This sequence of actions may be repeated to perform two-stage thermal modulation and comprehensive two-dimensional gas chromatography in the manner known in the prior art.

The temperature of the cold gas jets is typically −190 degrees Celcius, and is maintained by flowing the gas through a liquid nitrogen cooled coil prior to exit from the nozzle. To maintain such cold temperatures at the gas nozzle outlets, the use of a vacuum jacketed cryogenic transfer line is required. The cold gas nozzles are formed by flattening the ends of tubes exiting this cryogenic transfer line. With liquid nitrogen cooling, the modulator is capable of modulating all organic substances, including methane gas.

A gas chromatograph having the construction indicated in FIG. 1, and employing the present method of transverse thermal modulation produces excellent comprehensive two-dimensional gas chromatography (GC×GC), as indicated by an analysis of kerosene, as shown in the GC×GC chromatogram of FIGS. 3A–3D.

The experimental parameters used to obtain this chromatogram were as follows:

First Column: 4.0 meter long, $100\mu$ i.d., $3.5\mu$ film thickness, DB-1 Stationary Phase Second Column: 0.3 meter long, $100\mu$ i.d., $0.1\mu$ film thickness, BPX-50 Stationary Phase Modulator Tube: head of second column Temperature Program: 35° C. to 250° C. @ 2.39° C./minute Injector: Split/Splitless, Split Ratio 250:1, Head Pressure 18 psi, 275° C.

Detector: 285° C., Hydrogen Flow 70 cc/min, Air Flow 400 cc/min

Sample: Kersosene, neat, 0.1 ml injected

It is apparent from the foregoing that many variations of the current embodiment are possible.

Gas jets may be disrupted by a mechanically rotated baffle disposed between the jets and the modulator tube. Such an embodiment could produce high modulation frequencies.

Pulse timing can be varied to tune the thermal modulator. Valve control pulses may be overlapped to varying degrees. In such an embodiment, heating and cooling times of modulator stages would overlap, and the degree of overlap could be varied in order to tune the modulator performance.

Transverse thermal modulation is observed with an uncoated capillary tube in place of a capillary column 5a. In such an embodiment, thermal modulation is used to enhance the sensitivity of a conventional one-dimensional gas chromatograph. Sensitivity enhancement derives from focusing effects associated with thermal modulation. Sensitivity improvement by a factor of 7 or more is observed when the thermal modulation frequency is 2 Hz, and can be greater than a factor of 20 at lower modulation frequencies, which permit more chemical substances to accumulate into sharp chemical pulses.

In practice, the various components shown in FIG. 1 may be assembled into a compact device that modifies a conventional gas chromatograph.

Gas nozzles may be formed by flattening the ends of metal tubes, which may be brought through the top of the gas chromatographic oven, and caused to protrude thereinto. The modulator tube may be mounted with a clip located at the end of the nozzle assembly.

Nozzle assemblies can be swiveled mechanically at high speeds in order to achieve alternate heating and cooling of modulator stages. Even higher modulation frequencies can be attained by interrupting gas jets with a baffle rotated between the jet and the modulator tube. It is possible to achieve single stage thermal modulation by using only a single cooling nozzle on a single segment of capillary column, and permitting the stirred oven bath to heat the column ambiently when the cooling gas jet is disrupted or diverted.

It is apparent from the foregoing that the present invention has numerous advantages over prior art thermal modulators. All components used in the apparatus with which transverse thermal modulation is implemented are rugged and robust. Column alignment, which has posed operational difficulty with prior art mechanically swept heaters and coolers, is greatly simplified by the present invention, which entails clipping a segment of capillary column such that it is suspended into the paths of the gas jets. The present invention can eliminate the rotation or translation of heaters or coolers longitudinally along the column. Since the moving parts of the present invention are valve elements, and typically piloted valve elements, with low inertia and fast actuation times, thermal modulation at frequencies of 2 Hz or greater is readily achieved.

All these advantages accrue from the surprising fact that gas jets can rapidly heat and cool column segments even in the presence of a vigorously stirred oven air bath.

The present invention is summarized below. The present invention, among other things, relates to a method of thermally modulating a tubular member carrying a sample substance therethrough. The method comprises the steps of: (a) directing at least one gas stream toward said tubular member in a direction substantially transverse to the tubular member, wherein the temperature of the gas stream differs from the temperature of the tubular member; and (b) varying the gas flow rate of the at least one gas stream as a function of time to thermally modulate the tubular member The at least one gas stream is preferably supplied from a gas nozzle having a gas outlet, and the step of varying the gas flow rate comprises rotating a baffle between the gas outlet and the tubular member such that the baffle interrupts the flow of the at least one gas stream toward the tubular member.

The at least one gas stream may comprise two or more gas streams, each of which gas streams is supplied from a respective gas nozzle having a respective gas outlet, and each respective gas stream flowing substantially transversely to the tubular member, and wherein the method includes varying the gas flow rate of each respective gas stream as a function of time to produce multi-stage thermal modulation of the tubular member.

The present invention also relates to a method as described above wherein the gas flow rate is varied with a valve or with a mechanical diversion means.

The at least one gas stream may be supplied by at least one gas nozzle assembly, and the gas flow rate of the at least one gas stream may be varied by swiveling the gas nozzle assembly.

The method of the present invention can also involve repeating the thermal modulation of the tubular member in a manner that effects comprehensive multidimensional gas chromatography.

The method can also involve thermally modulating the tubular member effectively to modulate substances flowing through the tubular member that would be unretained under normal gas chromatographic operating temperatures.

The method can involve thermally modulating a tubular member effectively to modulate methane gas.

The apparatus of the present invention for thermal modulation comprises:

a tubular member for carrying a sample substance therethrough in a fluid medium;

a gas stream source for directing a gas stream toward said tubular member in a direction substantially transverse to the tubular member;

means for providing a gas stream supplied from the source with a temperature that differs from the temperature of the tubular member; and means for varying the gas flow rate of a gas stream supplied from the gas stream source as a function of time to thermally modulate the tubular member.

According to an embodiment of the present invention, the at least one gas stream source of the apparatus can include a gas nozzle having a gas outlet. In yet another embodiment, the means for varying the gas flow rate can include a rotatable baffle that can be rotated to interrupt a flow of the gas stream toward the tubular member. The apparatus can further comprise one or more additional gas stream sources, each for respectively directing a gas stream toward the tubular member in a direction substantially transverse to the tubular member, and/or one or more additional means for providing respective gas streams supplied from the respective additional sources with respective temperatures that differ from the temperature of the tubular member. Furthermore, the apparatus can include one or more additional means for varying the gas flow rate of the one or more respective additional gas streams supplied from the one or more additional respective gas stream sources, each as a function of time, to thermally modulate the tubular member.

The apparatus can include means for varying that includes a valve or a mechanical diversion means.

The gas stream source of the apparatus can include a gas nozzle assembly, and the means for varying can include means for swiveling the gas nozzle assembly.

The present invention is particularly well suited to operate with a tubular member that is a chromatographic column, for example, a gas chromatographic column or two chromatographic columns in communication with each other at an intersection wherein the gas stream source is positioned adjacent the intersection.

According to an embodiment of the present invention, the apparatus can include a stationary phase, within the tubular member, that is terminated within a thermal zone formed by the gas stream. The apparatus can include heated and cooled regions of the tubular member that are of unequal lengths.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of thermally modulating a tubular member carrying a sample substance therethrough, said method comprising the steps of:
   (a) directing two or more gas streams toward said tubular member in a direction substantially transverse to said tubular member, wherein the temperature of the two or more gas streams differs from the temperature of the tubular member; and
   (b) varying a gas flow rate of each of said two or more gas streams as a function of time to produce multi-stage thermal modulation of the tubular member,
   wherein each of said two or more gas streams is supplied from a respective gas nozzle having a respective gas outlet.

2. The method of claim 1, wherein said step of varying the gas flow rate comprises rotating a baffle between said respective gas outlet and said tubular member such that said baffle interrupts a flow of each of said two or more gas streams toward said tubular member.

3. The method of claim 1, wherein the gas flow rate of each of said two or more gas streams is varied with a valve.

4. The method of claim 1, wherein said gas flow rate of each of said two or more gas streams is varied with a mechanical diversion means.

5. The method of claim 1, wherein each of said two or more gas streams is supplied by at least one respective gas nozzle assembly, and the gas flow rate of each of said two or more gas streams is varied by swiveling said at least one respective gas nozzle assembly.

6. The method of claim 1, wherein the thermal modulation of the tubular member is repeated in a manner that effects comprehensive multi-dimensional gas chromatography.

7. The method of claim 1, wherein the thermal modulation effectively modulates substances flowing through the tubular member that would otherwise be unretained under normal gas chromatographic operating conditions.

8. The method of claim 1, comprising thermally modulating methane gas.

9. A method of thermally modulating a tubular member carrying a sample substance therethrough, said method comprising the steps of:
   (a) directing at least one gas stream toward said tubular member in a direction substantially transverse to said tubular member, wherein the temperature of the gas stream differs from the temperature of the tubular member; and
   (b) varying the gas flow rate of the at least one gas stream as a function of time to thermally modulate the tubular member,
   wherein said at least one gas stream is supplied from a gas nozzle having a gas outlet, and said step of varying the gas flow rate comprises rotating a baffle between said gas outlet and said tubular member such that said baffle interrupts the flow of said at least one gas stream toward said tubular member.

10. A method of thermally modulating a tubular member carrying a sample substance therethrough, said method comprising the steps of:
    (a) directing at least one gas stream toward said tubular member in a direction substantially transverse to said tubular member, wherein the temperature of the gas stream differs from the temperature of the tubular member; and
    (b) varying the gas flow rate of the at least one gas stream as a function of time to thermally modulate the tubular member,
    wherein said at least one gas stream is supplied by at least one gas nozzle assembly, and the gas flow rate of said at least one gas stream is varied by swiveling said gas nozzle assembly.

11. An apparatus for thermal modulation comprising:
    a tubular member for carrying a sample substance therethrough in a fluid medium;
    two or more gas stream sources for directing two or more respective gas streams toward said tubular member in a direction substantially transverse to said tubular member;
    means for providing said two or more respective gas streams supplied from said two or more gas stream sources with a temperature that differs from the temperature of the tubular. member; and
    means for varying a gas flow rate of said two or more respective gas streams supplied from said two or more gas stream sources as a function of time to thermally modulate the tubular member.

12. The apparatus of claim 11, wherein each of said two or more gas stream sources includes a respective gas nozzle having a respective gas outlet.

13. The apparatus of claim 11, wherein said means for varying the gas flow rate comprises a rotatable baffle that can be rotated to interrupt a flow of each of said two or more respective gas streams toward said tubular member.

14. The apparatus of claim 11, wherein said means for varying comprises a valve.

15. The apparatus of claim 11, wherein said means for varying comprises a mechanical diversion means.

16. The apparatus of claim 11, wherein each of said two or more gas stream sources comprises a respective gas nozzle assembly, and said means for varying comprises means for swiveling said respective gas nozzle assembly.

17. The apparatus of claim 11, wherein said tubular member is a chromatographic column.

18. The apparatus of claim 11, wherein said tubular member is a gas chromatographic column.

19. The apparatus of claim 11, wherein said tubular member comprises two chromatographic columns in communication with each other at an intersection, and each of said two or more gas stream sources are positioned adjacent said intersection.

20. The apparatus of claim 11, wherein a stationary phase is provided within said tubular member and said stationary phase is terminated within a thermal zone formed by one of said two or more respective gas streams.

21. The apparatus of claim 11, wherein said apparatus is provided with means to form at least one heated region of the tubular member and at least one cooled region of the tubular member, and wherein said at least one heated region is of an unequal length relative to a length of said at least one cooled region.

22. An apparatus for thermal modulation comprising:
    a tubular member for carrying a sample substance therethrough in a fluid medium;
    a gas stream source for directing a gas stream toward said tubular member in a direction substantially transverse to said tubular member;
    means for providing said gas stream supplied from said gas stream source with a temperature that differs from the temperature of the tubular member; and
    means for varying the gas flow rate of said gas stream supplied from said gas stream source as a function of time to thermally modulate the tubular member,
    wherein said means for varying the gas flow rate comprises a rotatable baffle that can be rotated to interrupt a flow of said gas stream toward said tubular member.

23. An apparatus for thermal modulation comprising:

a tubular member for carrying a sample substance therethrough in a fluid medium;

a gas stream source for directing a gas stream toward said tubular member in a direction substantially transverse to said tubular member;

means for providing said gas stream supplied from said gas stream source with a temperature that differs from the temperature of the tubular member; and means for varying the gas flow rate of said gas stream supplied from said gas stream source as a function of time to thermally modulate the tubular member, wherein said gas stream source comprises a gas nozzle assembly, and said means for varying comprises means for swiveling said gas nozzle assembly.

24. An apparatus for thermal modulation comprising:

a tubular member for carrying a sample substance therethrough in a fluid medium;

a gas stream source for directing a gas stream toward said tubular member in a direction substantially transverse to said tubular member;

means for providing said gas stream supplied from said gas stream source with a temperature that differs from the temperature of the tubular member; and means for varying the gas flow rate of said gas stream supplied from said gas stream source as a function of time to thermally modulate the tubular member, wherein said tubular member comprises two chromatographic columns in communication with each other at an intersection, and said gas stream source is positioned adjacent said intersection.

25. An apparatus for thermal modulation comprising:

a tubular member for carrying a sample substance therethrough in a fluid medium;

a gas stream source for directing a gas stream toward said tubular member in a direction substantially transverse to said tubular member;

means for providing said gas stream supplied from said gas stream source with a temperature that differs from the temperature of the tubular member; and means for varying the gas flow rate of said gas stream supplied from said gas stream source as a function of time to thermally modulate the tubular member, wherein a stationary phase is provided within said tubular member and said stationary phase is terminated within a thermal zone formed by said gas stream.

26. An apparatus for thermal modulation comprising:

a tubular member for carrying a sample substance therethrough in a fluid medium;

a gas stream source for directing a gas stream toward said tubular member in a direction substantially transverse to said tubular member;

means for providing said gas stream supplied from said gas stream source with a temperature that differs from the temperature of the tubular member; and means for varying the gas flow rate of said gas stream supplied from said gas stream source as a function of time to thermally modulate the tubular member, wherein said apparatus is provided with means to form at least one heated region of the tubular member and at least one cooled region of the tubular member, and wherein said at least one heated region is of an unequal length relative to a length of said at least one cooled region.

* * * * *